United States Patent [19]

Takahasi et al.

[11] 3,972,625
[45] Aug. 3, 1976

[54] MILK FAT CONTENT-MEASURING APPARATUS

[75] Inventors: Yoshiyuki Takahasi, Kanagawa; Shigenobu Kawawa, Machida, both of Japan

[73] Assignee: Anritsu Electric Co., Ltd., Tokyo, Japan

[22] Filed: Oct. 21, 1975

[21] Appl. No.: 624,544

Related U.S. Application Data

[63] Continuation-in-part of Ser. No. 451,932, March 18, 1974, abandoned.

[30] Foreign Application Priority Data

Mar. 31, 1973 Japan.............................. 48-36875

[52] U.S. Cl................................. 356/206; 23/258; 356/181; 356/208; 356/243
[51] Int. Cl.²................... G01N 21/22; G01N 33/04
[58] Field of Search........... 356/181, 201, 205, 206, 356/208, 243; 250/565, 575; 23/258

[56] References Cited
UNITED STATES PATENTS

| | | | |
|---|---|---|---|
| 2,752,815 | 7/1956 | Batchelor | 23/258 |
| 3,518,011 | 6/1970 | Rochte | 356/181 |
| 3,787,124 | 1/1974 | Lowy et al. | 356/205 |

*Primary Examiner*—Vincent P. McGraw
*Attorney, Agent, or Firm*—Edward H. Loveman

[57] ABSTRACT

An apparatus for measuring the fat content of milk includes an optical guide having two light passageways for guiding light delivered from a light source. One of said light passageways is provided with a cuvette through which the fat of milk flows. Disposed adjacent to the cuvette is an optical correction device, which includes an open window and at least one optical correction window. The optical correction window comprises a transparent glass plate over which there are uniformly formed a number of scratches each having such a dimension as is capable of giving an optical result corresponding to the milk fat particles.

8 Claims, 6 Drawing Figures

MILK FAT CONTENT-MEASURING APPARATUS

CROSS-REFERENCE TO RELATED APPLICATION

This is a continuation-in-part application of U.S. patent application Ser. No. 451,932 filed on Mar. 18, 1974, and now abandoned.

BACKGROUND OF THE INVENTION

This invention relates to an apparatus for optically measuring the fat content of milk and associated products.

The customary process of measuring the fat content of milk and associated products comprises the steps of dissolving the protein contained in milk, for example, in a solution of caustic soda to produce fat particles in a thermostat maintained at a prescribed temperature; unifying the fat particles generally having widely varying sizes under pressure in a homogenizer, followed by uniform dispersion; applying visible beams of light to the dispersed fat particles; and finally detecting beams of light permeating the fat particles and also those scattered thereby so as to determine the fat content of milk.

Where milk makers use the above-mentioned type of milk fat content-measuring apparatus at the site, it is necessary to examine periodically as well as quickly whether a value indicated by said measuring apparatus agrees with a prescribed milk fat content. However, where said measuring apparatus is used particularly for a long period, a source of light for projecting light on fat particles and a detector for detecting permeating beams of light often indicate deterioration of property with time or due to variations in the environmental conditions, for example, ambient temperature, thus giving rise to errors of measurement. To date, therefore, the Gerber or Babcock method has been adopted for correction of such errors of measurement. To this end, another method has also been developed which consists in supplying a measuring apparatus with the solution of a specific chemical in place of milk which is considered to give the same optical result as milk fat. However, a measuring apparatus based on the Gerber or Babcock method which require sulfuric acid should be handled with care and moreover takes a longer time than 30 minutes in correcting the results of measurement. Therefore, other persons than well-skilled operators can not properly adjust the operation of the measuring apparatus. Further, where the conventional milk fat-measuring apparatus is used, it is necessary to provide a correction device based on the Gerber or Babcock method nearby. On the other hand, the correction method of charging the solution of a chemical into the measuring apparatus in place of milk is likely to give rise to differences between the actual fat content and the prescribed value of the solution of a chemical, depending on the process of preparing said solution and the changes with time suffered by the solution, failing to attain the accurate correction of the milk fat content-measuring apparatus.

SUMMARY OF THE INVENTION

It is accordingly the object of this invention to provide a milk fat content-measuring apparatus equipped with an error-correcting device of simple construction.

According to an aspect of this invention, there is provided a milk fat content-measuring apparatus which comprises a source of light; an optical guide consisting of at least two light passageways for guiding light delivered from the source of light; and two photoelectric conversion devices disposed at the outlets of the respective light passageways of the optical guide, wherein one light passageway is provided with a cuvette through which the fat of milk passes and an optical correction device positioned adjacent to the cuvette, said optical correction device including an open window and at least one optical correction window having an optical result corresponding to a prescribed milk fat content; outputs from the two photoelectric conversion devices are supplied to an electric signal mixer through two corresponding amplifiers; and an output from the mixer is conducted to a gain controlling means connected to an indication type gauge.

When a milk fat content-measuring apparatus of the above-mentioned construction is put to practical application, the optical correction window having an optical result corresponding to a prescribed milk fat content is aligned with one of the two light passageways; the indication type gauge has its gain so controlled as to indicate a prescribed value; after said gain control, the open window is aligned with said one light passageway; the fat of milk is made to run through the cuvette; and a value indicated by the gauge is read.

The above-mentioned measuring apparatus can have its operation easily corrected, always attaining the accurate measurement of any milk fat content.

DETAILED DESCRIPTION OF THE INVENTION

Figure 1:
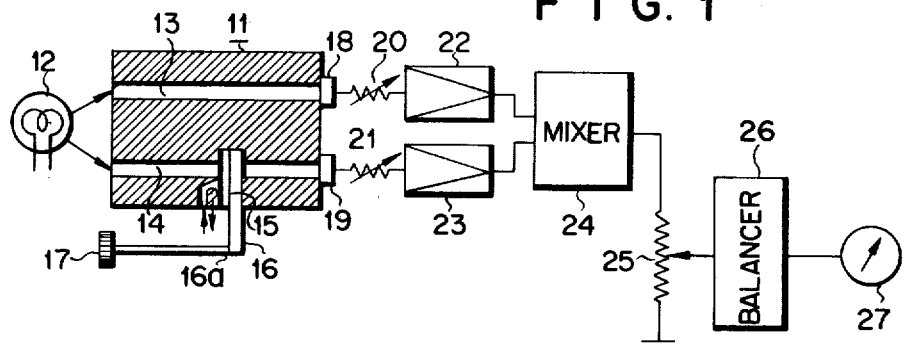
FIG. 1 is a block circuit diagram of a milk fat content-measuring apparatus according to an embodiment of this invention.
Figure 2:
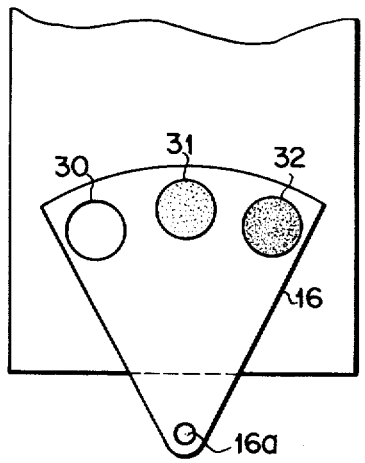
FIG. 2 is a plan view of an optical correction device included in the apparatus of FIG. 1.

Referring to FIG. 1 showing the subject milk fat content-measuring apparatus, an optical guide 11 is so disposed as to face a source of light 12. The object guide 11 has two light passageways 13 and 14 so constructed as to make no optical reflection. One light passageway 14 is provided with a cuvette 15 through which the fat of milk is conducted. Rotatably disposed adjacent to the cuvette 15 is an optical correction device 16, which is rotated by a rotatable knob 17 whose shaft is connected to a fulcrum 16a. Two photoelectric conversion devices 18, 19 are provided at the outlets of the respective light passageways 13, 14. Said photoelectric conversion devices 18, 19 are connected to amplifiers 22, 23 through the corresponding control resistors 20, 21. Outputs from the amplifiers 22, 23 are supplied to a mixer 24, which consists of a differential amplifier whose circuit is integrated or integrated dividing circuit. The output terminal of the mixer 24 is connected to a gain controlling device 25, an output from which is supplied to an indication type gauge 27 through a balancing circuit 26 of an adjustable indication needle.

The optical correction device 16 comprises of a segmental plate provided with three windows 30, 31, 32 almost equidistantly spaced from each other.

Figure 3:
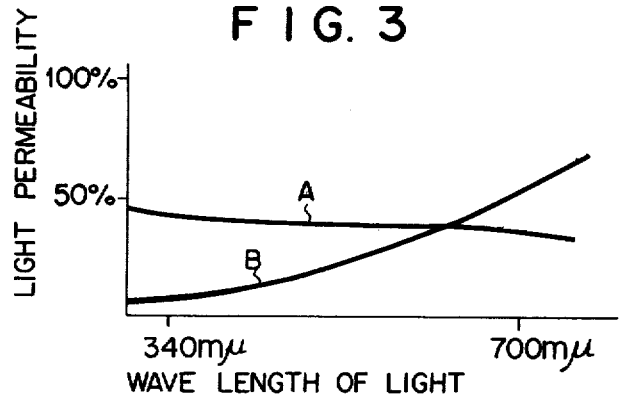
FIG. 3 is a graph illustrating the relation between a light permeability of milk and a wave of incident light.

The window 30 is an open type, whereas the windows 31, 32 are so formed as to have an optical result corresponding to the fat content of milk. In a solution wherein the fat component is present in the form of an emulsion such as a stock solution of milk, fat particles usually of uneven or ununiform size are dispersed, and when the turbidity of the water solution containing such size of fat particles is measured, there is almost no specific relationship between this turbidity and the fat content. In order to permit both to have a specific relationship, accordingly, it is necessary to make the particle size uniform. To this end, the milk fat content-measuring apparatus of this type is equipped with an equalizing means for reducing the milk fat particle size to below 1 $\mu$m. A solution dispersed uniformly with the milk fat particles of such reduced, equalized size is different in optical characteristic from a solution containing milk fat particles of large different size such as a stock solution of milk. This is apparent from the graphical diagram of FIG. 3. In FIG. 3, a curve A respresents the optical characteristic of a solution including of particles having a size of 2 $\mu$m (2 to 10 $\mu$m), and from this curve it is seen that the light permeability of the solution presents little variation with respect to the wavelength of light. A curve B represents the optical characteristic of a solution whose fat particles are reduced by the equalizing means to a uniform size of 1 $\mu$m or less, and according to this curve the light permeability of the solution is low in a region of small wavelength and becomes higher toward a region of large wavelength.

Since, in the case of actually measuring the fat content of milk, a milk sample has such an optical characteristic as shown by the curve B, there is the necessity of manufacturing the optical correction device 16 so as to conform with such optical characteristic of the milk sample.

To meet this demand, the correction windows 31, 32 are so constructed that their light permeability is high with respect to a large wavelength of light and low with respect to a small wavelength of light. In order that the correction windows 31, 32 may have such optical characteristic, an emery powder of not less than 1000 mesh, or preferably of 3000 to 4000 mesh is sprayed to a transparent glass plate to form thereover a number of scratches each having such a dimention, for example, 0.2 to 1.0 micron in depth as is capable of giving an optical result corresponding to milk fat particles. The number of the scratches is large enough to give an optical result corresponding to a prescribed milk fat content of, for example, 3 or 9 percent. The correction windows 31, 32 so constructed have substantially the same light permeability as that of milk, and as a result the milk fat content-measuring apparatus having such correction windows 31, 32 is capable of always exactly detecting the milk fat content of a milk sample irrespective of the wavelength of light.

That is to say, according to experimental results, the followings were confirmed. In a correction window wherein the scratches each 2 $\mu$m or more in depth are uniformly formed over the transparent glass plate, its light permeability is little varied with respect to the wavelength of incident light. However, as the scratches formed in the glass plate surface become shallow, the light permeability of the resulting correction window becomes low in a region of small wavelength and high in a region of large wavelength. When the scratch depth is decreased to 0.2 to 1 $\mu$m, the resulting correction window has such an optical characteristic as shown by the curve B in FIG. 3, in other words, the same optical characteristic as that of, for example, an ordinary milk including fat particles having a size of 1 $\mu$m or less. When it is desired to uniformly form scratches each having a depth of 0.2 to 1 $\mu$m, an abrasive material of, for example, emery powder, alumina powder, or silicon carbide powder has only to be sprayed onto the transparent glass plate surface.

Figure 4:
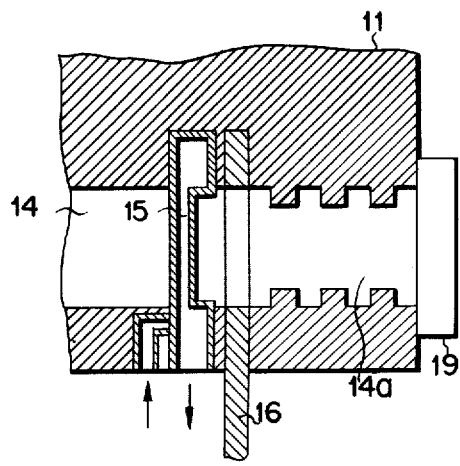
FIG. 4 is a fractional sectional view of said optical correction device provided with the cuvette and a plurality of windows.

The cuvette 15 is so shaped as to protrude inward in the central portion as shown in FIG. 4. This shape enables the fat of milk to be uniformly distributed during passage through the cuvette 15, attaining the accurate measurement of said fat content. The inner peripheral wall of the outlet portion 14a of the light passageway 14 is provided with inwardly extending projections as illustrated in FIG. 4 so as to enable light beams scattered by particles of milk fat to be effectively brought to the photoelectric conversion device 19.

There will now be described the operation of the subject milk fat content-measuring apparatus constructed as described above.

Before the operation of the measuring apparatus is corrected, the interior of the cuvette is first cleaned by a suitable washing solution. Thereafter, while transparent water, for example, is made to flow through the cuvette 15, the optical correction device 16 is rotated by operation of the knob 17 so as to align the first optical correction window 31 with the light passageway 14. Next, when the light source 12 is operated, light is conducted therefrom to the light passageways 13, 14. The light traveling through the light passageway 13 directly reaches the first photoelectric conversion device 18 to be converted into a first electric signal. On the other hand, the light carried through the light passageway 14 is brought to the second photoelectric conversion device 19 through the water running through the cuvette 15 and the first optical correction window 31 to be converted into a second electric signal.

The first and second electric signals are conducted to the mixer 24 through the fine adjustment variable resistors 20, 21 and amplifiers 22, 23. The mixer 24 is supplied with the first electric signal corresponding to a source of light changing due to various causes and consequently usable as a referential signal for correction of the source of light and also with the second electric signal corresponding to such an amount of light as shows an optical result exactly representing a prescribed milk fat content of, for example, 3 percent. If, in this case, the indication needle 27 happens to fail accurately to show the prescribed milk fat content of 3 percent, then the needle is set to a scale graduation of 3 percent by means of the gain controlling device and the balancing circuit.

Next, the knob 17 of the optical correction device 11 is rotated to align the second optical correction window 32 with the light passageway 14, thereby detecting whether the indication needle 27 accurately shows the prescribed milk fat content of 9 percent previously set through the second optical correction window 32. If the indication needle 27 does not give a value of 9 percent, the needle 27 is set to a scale graduation of 9 percent by adjusting the gain controlling device 25 and balancing circuit 26. As mentioned above, the operation of the subject milk fat content-measuring apparatus may be corrected by reference to either of the aforesaid two percentages. If, however, correction is made twice on the basis of two different percentages, then said correction will be rendered extremely accurate.

When measurement is actually made of the fat content of a given milk sample, the open window 30 of the optical correction device 16 is aligned with the passageway 14 and the fat of said milk sample is introduced into the cuvette 15. Then a value given by the indication needle 27 represents the exact fat content of said milk sample.

Figure 5:
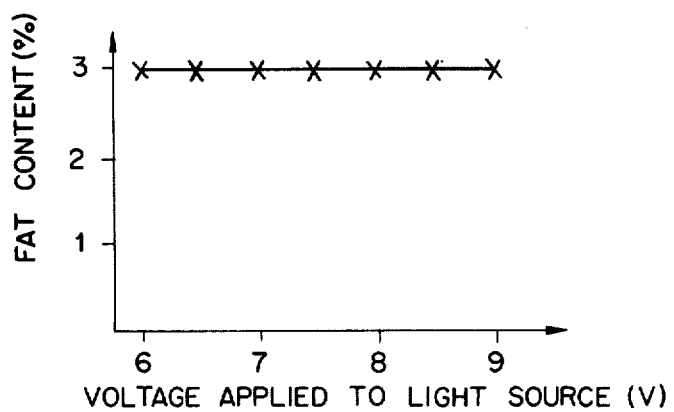
FIG. 5 graphically shows milk fat contents and the relationship between levels of voltage impressed on a source of light.

As apparent from FIG. 5 showing readings from the indication needle 27 corresponding to varying levels of voltage impressed on the source of light 12, the milk fat content-measuring apparatus of this invention does not present any change in the indicated value of the same milk fat content, but always accurately shows said content, regardless of variations in the source voltage, once the operation of said apparatus is properly corrected.

As mentioned above, the milk fat content-measuring apparatus of this invention can have its operation corrected quickly and accurately, even though the optical measurement system may be affected by the deterioration with time of its property or variations in ambient temperature.

Figure 6:
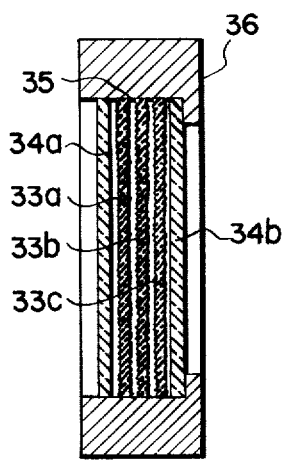
FIG. 6 is a side sectional view of the optical correction device according to another embodiment of the invention.

If each of the above-mentioned correction windows 31, 32 is constituted by a plurality of thin glass plates each having the above-mentioned scratches, it will be possible to measure the milk fat content more exactly. That is to say, as shown in FIG. 6, for example three optical transparent glass plates 33a, 33b and 33c each having scratches each of depth of 0.2 to 1 $\mu$m uniformly formed over the surface thereof are laminated, and this laminated mass is sandwiched from outside by two transparent holding glass plates 34a, 34b whose surfaces are flat, and the peripheral edge portions of these glass plates 33a to 33c, 34a and 34b are bonded by an adhesive to a holding frame 36 and held thereby.

The use of the multiple laminate-structural correction window makes it possible to obtain substantially the same optical characteristic as that of, for example, milk. That is, in the case of a single layer-structural correction window, light diffusion is effected only by scratches formed over the surface of the correction window. However, the fat particles in the milk are uniformly distributed in the milk and light is diffused by these uniformly distributed fat particles. Accordingly, the light diffusion by the fat particles of milk is different in degree from the light diffusion by the scratches over one surface of the correction window. This difference in respect of the degree of light diffusion is removed by using the multiple laminate-structural correction window.

What we claim is:

1. A milk fat content-measuring apparatus which comprises a source of light; an optical guide having at least first and second light passageways for guiding light delivered from the source of light; a cuvette provided in the first light passageway of the optical guide so as to conduct the fat of a milk sample being examined; an optical correction device received in the first light passageway adjacent to the cuvette, formed of an open window and at least one optical correction window including at least one transparent glass plate over which there are uniformly formed a number of scratches each having such a dimension as is capable of giving an optical result corresponding to milk fat particles, and so constituted as to cause these windows to be selectively aligned with the first light passageway; a first photoelectric conversion device disposed at the outlet of the first light passageway so as to convert the source light guided by said passageway through the cuvette and optical correction device into an electric signal; a second photoelectric conversion device provided at the outlet of the second light passageway so as to convert the source light traveling through said passageway directly into an electric signal; an electric signal mixer supplied with output signals from the first and second photoelectric conversion devices; and an indication type gauge for indicating a value based on an output from the mixer, whereby the measuring apparatus can have its operation corrected accurately to show a prescribed milk fat content on said gauge.

2. A measuring apparatus according to claim 1 wherein the optical correction device includes an open window, a first optical correction window comprising a transparent glass plate over which there is uniformly formed scratches of a number large enough to give an optical result corresponding to a first prescribed milk fat content and a second optical correction window comprising a transparent glass plate over which there is uniformly formed scratches of a number large enough to give an optical result corresponding to a second prescribed milk fat content.

3. A measuring apparatus according to claim 2 wherein the first optical correction window indicates an optical result corresponding to a milk fat content of 3 percent and the second optical correction window gives an optical result corresponding to a milk fat content of 9 percent.

4. A measuring apparatus according to claim 1 wherein the first light passageway of the optical guide has the inner peripheral wall of its outlet portion provided with inwardly extending projections.

5. A measuring apparatus according to claim 1 wherein the cuvette has its central portion projected inward.

6. A measuring apparatus according to claim 1 wherein a variable resistor and indication needle-balancing device are connected in series between the mixer and indication type gauge.

7. A measuring apparatus according to claim 1 wherein said optical correction window comprises three laminated transparent glass plates, over each of which there are uniformly formed a number of scratches each having such a dimension as is capable of giving an optical result corresponding to milk fat particles.

8. A measuring apparatus according to claim 1 wherein said scratches each are 0.2 to 1 $\mu$m deep.

* * * * *